United States Patent [19]

Ali et al.

[11] Patent Number: 5,521,222

[45] Date of Patent: *May 28, 1996

[54] TOPICAL OPHTHALMIC PHARMACEUTICAL VEHICLES

[75] Inventors: Yusuf Ali, Fort Worth, Tex.; Kenneth W. Reed, Lawrenceville, Ga.

[73] Assignee: Alcon Laboratories, Inc., Fort Worth, Tex.

[*] Notice: The term of this patent shall not extend beyond the expiration date of Pat. No. 5,461,081.

[21] Appl. No.: 356,044

[22] Filed: Dec. 14, 1994

Related U.S. Application Data

[63] Continuation of Ser. No. 170,438, Dec. 20, 1993, Pat. No. 5,461,081, which is a continuation of Ser. No. 913,110, Jul. 14, 1992, abandoned, which is a continuation-in-part of Ser. No. 414,550, Sep. 28, 1989, abandoned.

[51] Int. Cl.$^6$ ........................ A61K 31/715; A61K 47/00
[52] U.S. Cl. ........................ 514/772.5; 514/54; 514/781; 514/782; 514/912
[58] Field of Search ........................ 514/772.3, 54, 514/781, 782, 912

[56] References Cited

U.S. PATENT DOCUMENTS

| | | | |
|---|---|---|---|
| 4,136,173 | 1/1979 | Pramoda et al. | 424/177 |
| 4,616,012 | 10/1986 | Neustadt et al. | 514/223.2 |
| 4,638,059 | 1/1987 | Sutherland | 536/121 |
| 4,783,444 | 11/1988 | Watkins et al. | 514/912 |
| 4,861,760 | 8/1989 | Mazuel et al. | 514/54 |
| 4,911,920 | 3/1990 | Jani et al. | 424/78 |
| 5,188,826 | 2/1993 | Chandrasekaran et al. | 424/78.04 |
| 5,192,535 | 3/1993 | Davis et al. | 424/78.04 |
| 5,212,162 | 5/1993 | Missel et al. | 514/54 |

FOREIGN PATENT DOCUMENTS

| | | |
|---|---|---|
| 0495421A1 | 7/1992 | European Pat. Off. . |
| 2007091 | 5/1979 | United Kingdom . |
| WO89/06964 | 8/1989 | WIPO . |
| WO91/19481 | 12/1991 | WIPO . |

OTHER PUBLICATIONS

B.F. Goodrich Carbopol® Resins—Product Information.
"Vehicle effects on ophthalmic bioavailability: the influence of different polymers on the activity of pilocarpine in rabbit and man," *J. Pharm. Pharmacol.*, vol. 34, pp. 464–466, 1982.

*Primary Examiner*—Zohreh Fay
*Attorney, Agent, or Firm*—Patrick M. Ryan; Sally S. Yeager

[57] ABSTRACT

Ophthalmic pharmaceutical vehicles which become viscous on contacting the eye are disclosed. Ophthalmic compositions of the vehicle and a pharmaceutically active drug are also disclosed.

8 Claims, No Drawings

TOPICAL OPHTHALMIC PHARMACEUTICAL VEHICLES

This application is a continuation of application Ser. No. 08/170,438 filed on Dec. 20, 1993, now U.S. Pat. No. 5,461,081 which is a continuation of prior application, Ser. No. 07/913,110 filed Jul. 14, 1992, now abandoned which is a continuation-in-part of application Ser. No. 07/414,550, filed Sep. 28, 1989, now abandoned.

BACKGROUND OF THE INVENTION

This invention is directed to liquid ophthalmic pharmaceutical vehicles which become viscous on contacting the eye. This invention also relates to topical ophthalmic compositions comprising the vehicle and a pharmaceutically active drug.

It is known that the addition of viscous or visco-elastic polymers to an eye drop pharmaceutical composition, will increase the viscosity of the composition. This is usually desirable on the premise that an increased vehicle viscosity enhances drug delivery and duration of action; see, for example, *J. Pharm. Pharmacol.*, Vol.34, pp.464–466 (Jan. 7, 1982). However, it is frequently advantageous to administer ophthalmic compositions as a drop, that is, an aqueous solution or suspension rather than a thick, viscous gel or ointment which can be messy and may tend to blur vision. In addition, non-droppable compositions can present problems with patient compliance, especially with the elderly.

The present invention provides for ophthalmic compositions which can be administered as a drop, but whose viscosity increases upon instillation into the eye so that the composition provides for relatively better drug delivery and duration of action, referred to herein as bioavailability, of drug over aqueous compositions whose viscosity does not increase upon instillation.

SUMMARY OF THE INVENTION

This invention relates to ophthalmic pharmaceutical vehicles and compositions comprising the vehicle and a pharmaceutically active drug in which the vehicle comprises a charged polymer and oppositely charged electrolytes or molecules, hereinafter referred to collectively as "electrolytes", which can be administered as a drop and upon instillation, gel. The polymer can be negatively charged, such as a carboxyvinyl polymer, in which case the vehicle will include positively charged electrolytes, such as calcium. Or the polymer can be positively charged and then negatively charged electrolytes are used in the vehicle.

The vehicles of this invention can be used in composition with pharmaceutically active drugs. The term "drug", as used herein, means any therapeutic agent that is desirable to deliver to the eye. There is no limitation on the type of drug which can be incorporated into the compositions disclosed herein. The drugs can be charged, uncharged, water soluble or insoluble.

This invention is also directed to methods for delivering drugs to the eye by topical administration of the compositions disclosed herein.

DETAILED DESCRIPTION OF PREFERRED EMBODIMENTS

The vehicles disclosed herein comprise a charged polymer and oppositely charged electrolytes. Without intending to be bound by any theory, it is understood that the vehicle's viscosity is dramatically increased due to the decrease in electrolyte concentration when the vehicle is administered to the eye. The concentration of the polymer and electrolytes in the vehicle is optimal when a small change in electrolyte concentration will result in a dramatic increase in vehicle viscosity. The small change in electrolyte concentration on instillation results either by the electrolytes being taken up by the cells in the eye or by diffusing out of the polymer vehicle and eliminated in tear fluid. In either case, the concentration of electrolytes in the vehicle is reduced and the vehicle viscosity increases.

Accordingly, polymers which can be used in the vehicle disclosed herein include any nontoxic charged water soluble polymer. These polymers can either be negatively or positively charged. Typically, negatively charged polymers will include, but are not limited to, carboxy vinyl polymers, such as Carbopol$^R$, sodium carboxy methylcellulose, pectin gelatin (Type B) sodium hyaluronic acid, acacia, calcium carboxy methylcellulose, sodium alginate and polystyrene sulfonic acid (PSSA). These polymers are used in the vehicles at concentrations from about 0.2 to about 10.0 weight percent (wt. %) preferably about 1.0–3.0 wt. %.

Electrolytes which are used in conjunction with the charged polymers will be either cations or anions depending on the charged polymer being used. If negatively charged polymers are being used in the vehicle the electrolytes which are used to provide for the changing viscosity upon instillation will be positively charged. These cations will typically be $Na^+$, $K^+$, $Mn^{++}$, $Ca^{++}$, $Mg^{++}$, $Fe^{++}$, $Fe^{+++}$, $Li^+$, $Zn^{++}$ and $Be^{++}$. In addition, positively charged organic ions can be used, for example, lysine. HCl, argenine. HCl and histadine. HCl. These electrolytes will typically be present at a concentration of between 0.01 and 1.0 wt. %.

If a positively charged polymer is used, such as gelatin (Type A) or polyvinyl amine, the electrolyte used in conjunction therewith to provide for viscosity changes will be an anion. These anions will typically be $PO_4^{-3}$, $HPO_4^{-2}$, $H_2PO_4^-$, $I^-$, $Cl^-$, $F^-$, $SO_4^{-2}$ and other negatively charged organic ions. Again, the polymer concentration will range from about 0.2–10.0 wt. % and the electrolytes will typically be present at a concentration of between about 0.01 wt. % to about 1.0 wt. %.

The concentrations of the polymers and corresponding electrolytes are adjusted to provide for compositions in which the viscosity is such that the composition can be administered as a drop topically. Thus, prior to instillation in the eye, the viscosity will be between about 200 to about 2000 cps.; then, on instillation, the viscosity of the composition will increase to greater than 2000 cps. This is accomplished by adjusting the concentrations of the polymer and electrolyte, in conjunction with any other ingredients, such as a drug, such that only a small change in the electrolyte concentration, which will occur upon instillation in the eye, will provide for a large increase in viscosity. The resulting compositions allow for the delivery of a drug in drop form, but provide for enhanced drug delivery due to the compositions' increased viscosity once in the eye.

Pharmaceutically active drugs can be included in the vehicles of the present invention to make ophthalmic compositions. Drugs which can be delivered in vehicles of the present invention include, but are not limited to, steroids, growth factors, antioxidants, aldose reductase inhibitors, non steroidal antiinflammatories, immunomodulators, antiallergics, antimicrobials, and beta-blockers. The ophthalmic compositions are formulated by adjusting the concentrations of the chosen polymer and electrolyte so that the compositions are administrable as drops and gel on instillation. The concentrations of the polymer and corresponding electrolyte are dependant upon the nature of the polymer itself, the nature of the drug/polymer charge interaction or lack thereof and the desired amount of drug retention time in the eye.

In addition to the principal active ingredients, the vehicles and compositions of the present invention may further comprise various formulatory ingredients, such as antimicrobial preservatives and tonicity agents. For example, antimicrobial preservatives include: benzalkonium chloride, thimerosal, chlorobutanol, methylparaben, propylparaben, phenylethyl alcohol, EDTA, sorbic acid, POLYQUAD and other agents equally well known to those skilled in the art. Such preservatives, if employed, will typically be used in an amount from about 0.0001 wt. % to 1.0 wt. %. Suitable agents which may be used to adjust tonicity or osmolality of the compositions include: mannitol, dextrose, glycerine and propylene glycol. If used, such agents will be employed in an amount of about 0.1 wt. % to 10.0 wt. %. However, preferable composition of the present invention will not include preservatives or tonicity agents which are known to adversely affect or irritate the eye, particularly the cornea.

This invention is also directed to methods for delivering pharmaceutically active drugs to mammals' eyes, particularly human eyes. According to the invention, drugs can be delivered to the eye by topically administering compositions comprising the vehicles disclosed herein and a drug.

The following examples are topical ophthalmic vehicles or compositions which can be administered to the eye as a drop and which gel in the eye upon instillation.

EXAMPLE 1

| Ingredient | Weight Percent |
| --- | --- |
| Carbopol 934P | 0.30 |
| Calcium chloride | 0.045 |
| Mannitol | 4.50 |
| NaOH | pH 7.2 ± 0.2 |
| Purified water | q.s. 100% |

Preparation 15 g of 2% Carbopol 934P were added to a 150 ml beaker containing a stir bar. 4.0 g of calcium chloride and 4.5 g of mannitol were added and the solution was stirred well. Purified water was added to about 80% of the 100 g batch weight and the pH was adjusted to 7.2±0.02 with sodium hydroxide. Purified water was added to bring final weight to 100 g.

The vehicles of Examples 2, 3, and 4 were prepared in the manner set forth in Example 1.

EXAMPLE 2

| Ingredient | Weight Percent |
| --- | --- |
| Carbopol 934 P | 0.40 |
| Calcium chloride | 0.10 |
| Mannitol | 4.00 |
| NaOH | pH 7.2 ± 0.2 |
| Purified water | q.s. 100% |

EXAMPLE 3

| Ingredient | Weight Percent |
| --- | --- |
| Carbopol 934P | 0.40 |
| Calcium chloride | 0.05 |
| Lysine HCl | 0.225 |
| Mannitol | 4.00 |
| NaOH | 7.2 ± 0.2 |

-continued

| Ingredient | Weight Percent |
| --- | --- |
| Purified Water | q.s. 100% |

EXAMPLE 4

The following formulation represents the preferred vehicle of the present invention.

| Ingredient | Weight Percent |
| --- | --- |
| Carbopol 934P | 1.00 |
| Calcium Chloride | 0.40 |
| Mannitol | 3.00 |
| KOH | pH 7.2 ± 0.2 |
| Purified Water | q.s. 100% |

EXAMPLE 5

The following formulation prepared and represents the preferred composition of the invention.

| Ingredient | Weight Percent |
| --- | --- |
| Betaxolol HCl | .28 |
| Carbopol 934P | 1.00 |
| Calcium Chloride | .75 |
| Mannitol | 1.5 |
| Benzalkonium Chloride | 0.01 |
| EDTA | .05 |
| pH | 7.2 |
| Purified Water | q.s. 100% |

We claim:

1. A topical ophthalmic vehicle comprising: a water soluble carboxy vinyl polymer and calcium ions at concentrations such that the vehicle is administrable as a drop and gels upon instillation as a result of the migration Of calcium ions out of the vehicle.

2. The vehicle of claim 1 wherein the polymer concentration is between about 0.2 and about 10 wt. %.

3. The vehicle of claim 1 wherein the calcium ion concentration is between about 0.01 and 1.0 wt. %.

4. A topical ophthalmic composition comprising: a vehicle comprising a water soluble carboxy vinyl polymer, calcium ions, and a pharmaceutically active drug, the polymer and calcium ions present at concentrations such that the composition is administrable as a drop and gels upon instillation as a result of the migration of calcium ions out of the vehicle.

5. The composition of claim 4 wherein the polymer concentration is between about 0.2 and 10.0 wt. %.

6. The composition of claim 4 wherein the calcium ion concentration is between about 0.01 and 1.0 weight percent.

7. The composition of claim 4 wherein the pharmaceutically active drug is betaxolol.

8. A method of delivering a drug to the eye, which comprises: topically administering a composition comprising a water soluble carboxy vinyl polymer and calcium ions at concentrations such that the composition is administratable as a drop and gels upon instillation as a result of the migration of calcium ions out of the composition.

* * * * *